United States Patent [19]

Chrisman et al.

[11] Patent Number: 4,697,546
[45] Date of Patent: Oct. 6, 1987

[54] METHOD FOR PRODUCTION OF TETRAPLOID CHANNEL CATFISH

[75] Inventors: Charles L. Chrisman, West Lafayette, Ind.; Christopher A. Bidwell, Davis, Calif.; George S Libey, Lafayette, Ind.

[73] Assignee: Purdue Research Foundation, West Lafayette, Ind.

[21] Appl. No.: 868,734

[22] Filed: May 30, 1986

[51] Int. Cl.⁴ ............................................ A01K 61/00
[52] U.S. Cl. ...................................................... 119/3
[58] Field of Search ................................. 119/1, 2, 3

[56] References Cited

U.S. PATENT DOCUMENTS 4,489,674 12/1984 Wolters et al. ........................ 119/3

FOREIGN PATENT DOCUMENTS 0013336 1/1983 Japan ....................................... 119/3

OTHER PUBLICATIONS

*Trans. Am. Fish. Soc.*, 110 (1981), 310–312.
*Trans. Am. Fish. Soc.*, 111 (1982), 102–105.
*Can. J. Fish. Aquat. Sci.*, 40 (1983), 2040–2043.
*Aquaculture*, 35 (1983), 125–134.
*Reprod. Nutr. Develop.*, 20 (1980), 727–733.
*J. Fish Biol.*, 17 (1980), 667–671.
*Aquaculture*, 36 (1984), 359–367.
*J. Fish. Biol.*, 7 (1975), 519–528.
*Trans. Am. Fish. Soc.* 110 (1981), 546–549.
*Reprod. Nutr. Develop.*, 22 (1982), 569–574.
*Cytobios*, 18 (1978), 201–234.
*Chromosoma* (Berlin), 51 (1975), 125–133.
*Aquaculture*, 29 (1982), 305–309.
*Aquaculture*, 51 (1985), 25–32.
Abstract: Cytogenetic and Cell Biology Presentations, Am. Diary Assn. Annual Mtg, U. of Illinois, Champaign, Urbana, Jun. 11, 1985.
Genetics in Aquaculture, 2d International Symposium, U. of Cal., Davis, Poster Session, Jun. 23–28, 1985.
*J. Exp. Zoology*, 210 (1979), 137–143.
*Aquaculture*, 36 (1984), 111–126.
*Aquaculture*, 35 (1983), 163–169.
44th Midwest Fish Wildlife Conf., Milwaukee WI, (1982), Abstr. No. 49.
Polyploidy: *Biological Relevance* (W. Lewis ed.) Plenum Press, NY, 3–15.
Polyploidy: *Biological Relevance* (W. Lewis ed.) Plenum Press, NY, 17–144.
Abstract: Adult Triploids in a Rainbow Trout Family, *Genetics* 93: 961–973, Dec. 1979.
*Aquaculture*, 10 (1977), 65–74.

*Primary Examiner*—Robert P. Swiatek
*Assistant Examiner*—Richard T. Price

[57] ABSTRACT

A method for the induction of tetraploidy in channel catfish by heat-shocking fertilized eggs is described. Fertilized catfish eggs are treated after a preliminary incubation period and prior to first cell division cleavage by immersing the fertilized eggs in water at a temperature of about 40° C. to about 43° C. for a temperature-dependent period of time ranging from about 1 to about 4 minutes. Incubation of the heat-shocked eggs allows maturation to tetraploid catfish fry. Breeding of tetraploid catfish with normal diploids produces rapid growing triploid offspring.

8 Claims, 4 Drawing Figures the
METHOD FOR PRODUCTION OF TETRAPLOID CHANNEL CATFISH

FIELD OF THE INVENTION

This invention is a method for the production of a tetraploid channel catfish. This method has the potential to increase the efficiencies and quality of commercial catfish production.

BACKGROUND OF THE INVENTION

Channel catfish (*Ictalurus punctatus*) are widely cultured in commercial fisheries because they are easily managed and have good food quality. Although much research has been performed on raising, stocking, and increasing the nutrition of channel catfish, little research has been directed toward genetic improvements that would increase its value as a cultured species.

One genetic improvement that provides benefits to fish culture is the production of triploid individuals. Triploidy is one type of polyploidy which may be generally described as a specimen with three complete sets of chromosomes versus the usual two sets of chromosomes. A triploid condition has been shown to be beneficial to commercial catfish production because triploid catfish grow larger and exhibit better feed conversion than diploid full-sibs.

Triploid channel catfish have been found to be sterile, however, and natural spontaneous triploidy in fish is rare. Thus, alternative methods for producing triploidy have been developed. For example, triploidy has been induced in certain fish species by cold-shocking fertilized eggs. U.S. Pat. No. 4,489,674 describes a method for 100% triploid conditioning by cold-shocking fertilized eggs at about 5° C. for about one hour approximately five minutes after fertilization.

Tetraploidization and mating tetraploid channel catfish with normal diploids to produce triploid offspring provides an improved method of producing triploidy, as compared to previous cold-shock treatment methods. Such previous triploidization techniques requiring hormonal treatment, sperm and egg handling, and cold shocks are not practical for commercial catfish production because of the time and labor required to produce enough fingerlings for grow-out ponds.

Studies have been made concerning the induction of tetraploid condition by thermal shock during early embryonic development. When heat shocks are applied shortly before first cleavage division, cytokinesis is inhibited. Zygotes undergo two genomic replications with only one cytoplasmic division. C. L. Rieder and A. S. Bajer reported that heat shocks cause depolymerization of tubulin polymers that form the microtubules essential for the formation of the spindle apparatus ("Effect of Elevated Temperature on Spindle Microtubules and Chromosome Movement in Cultured Newt Lung Cells", *Cytobios*, 18:201-234, 1978). G. Gaillard and A. Jaylet reported in "Mechanisme Cytologique de la Tetraploidie Experimentale Chez la Triton *Pleurodeles waltlii* Michach," *Chromosoma (Berlin)*, 38:173-184, 1975, that heat shocks are thought to inhibit spindle formation and aster movement.

The use of heat-shocks to induce tetraploidy in *Tilapia aurea* and rainbow trout, *Salmo gairdneri*, has been reported in R. J. Valenti, "Induction of Polyploidy in *Tilapia aurea* (Steindachner) by Means of Temperature Shock" *J. Fish. Biol.*, 7:519-528, 1975; G. H. Thorgaard et al. "Polyploidy Induced by Heat Shock in Rainbow Trout" *Trans. Am. Fish Soc.*, 110:546-550 (1981); and D. Chourrout, "Tetraploidy Induced by Heat Shocks in Rainbow Trout *Salmo gairdneri*" *R. Reprod. Nutr. Develop.*, 22:569-574, 1982. Resultant embryos, however, were frequently abnormal and at 18 months, no tetraploid rainbow trout were found in a heat-shock group that had produced the tetraploid embryo.

It is, therefore, an object of this invention to provide a method for producing tetraploid channel catfish having little or no anatomical abnormalities in embryos or in growing fry.

It is a further object of this invention to increase the hatchability and the percentage tetraploidy in channel catfish.

THE DRAWINGS

SUMMARY OF THE INVENTION

The present invention is directed to a method for induction of tetraploidy in channel catfish. The method comprises the steps of fertilizing an egg from a female channel catfish, incubating said fertilized egg for a first period of time, heat shocking said fertilized egg at a temperature of about 40° to about 43° for a time period of up to about four minutes, and incubating the heat-shocked egg until it matures to a tetraploid catfish fry.

The first period of time for incubation of the fertilized egg ranges from the time required for first cell division cleavage of the fertilized egg and a time about ten minutes less than said time required for first cell division cleavage. The first period of time for incubation is dependent to some extent on the incubating temperature. At a typical incubation temperature of about 27° C. the first incubation period is about 80 to about 90 minutes following egg fertilization. Ideally incubation is conducted in aerated flowing water.

The duration of the heat shock treatment of the fertilized egg following the first incubation period is typically no longer than four minutes and dependent on the heat shock treatment temperature. At temperatures of about 42° to about 43° C., duration of heat shock should be no more than about one minute. At the preferred heat shock temperature of about 41° C., a treatment time of about three to about four minutes is preferred for optimum production of tetraploid catfish embryos.

Tetraploid catfish of the present invention are useful for the production of rapid growing triploid catfish by breeding with normal diploids.

DETAILED DESCRIPTION OF THE PREFERRED EMBODIMENT OF THE INVENTION

The Method

Two gravid female channel catfish were placed in a 423-1 rectangular raceway maintained at 27° C. by flow through circulation of heated well water. One half of the raceway was covered with black plastic to simulate a spawning container. The fish were induced to ovulate by administration of carp pituitary extract (CPE) in two injections. A priming injection of 2 mg/kg CPE was followed 12 hours later by a resolving injection of 9 mg/kg CPE. A male was placed in the raceway with each female after the first injection of CPE.

When the fish began ovulating, the eggs were hand-stripped and fertilized with sperm from minced testes of donor males of the same species. Female 1 was stripped for 2 minutes and time zero of fertilization was initiated after the first minute of stripping. Female 2 was killed and the eggs were removed directly from one ovary. Time zero of fertilization started one minute after all eggs were removed from the ovary.

Figure 1:
FIG. 1 is a microphotograph of a fertilized catfish egg after first cleavage division.

For each female, fertilized eggs were divided evenly between 52 egg baskets and incubated at 27° C. in aerated well water prior to heat shock. Five batches of fertilized eggs were observed for first cleavage. Cleaved cells were first visible at 90 minutes postfertilization at 27° C. (FIG. 1). Development of channel catfish eggs was not synchronous with two, four, and eight cell stages visible between 90 and 120 minutes postfertilization.

Groups of eggs were treated starting at 80, 85, or 90 minutes postfertilization. Each group was shocked at either 40° C., 41° C., 42° C., or 43° C. for durations of 1, 2, 3, or 4 minutes. Earlier experiments showed that temperatures of 44° C. or higher were completely lethal in shocks of 1 minute or longer. All treatement combinations were administered to the eggs of each female. Four baskets of control eggs were not heat-shocked.

After treatment, the eggs were returned to the incubation tank, allowed to water harden for four hours, and transferred to a hatching tank for incubation at 27° C. The eggs from female 2 were placed in iron-filtered water after water hardening. Prophylactic measures to prevent fungal growth were started at 24 hours postfertilization. A 10 minute bath in a 1:100 dilution of Argentyne, manufactured by Argent Laboratories, Rewood, Wash. was administered at 12 hour periods until day 4 of incubation.

Chromosome counts to determine ploidy were performed on embryo tissue. Embryos were dissected out of their shells and placed in 0.05% colchicine for 6 to 8 hours. Each embryo was cut into three pieces and placed in 0.25% potassium chloride hypotonic solution for 40 minutes. Embryos were fixed in two changes of 3:1 methanol-acetic acid and dissociated in 50 percent acetic acid in water. Cell suspensions were placed on warm slides, stained for 20 minutes in 4% Giemsa in pH 6.5 Giordano buffer. Metaphase plates were counted for each individual at 900 to 1,000X. The plates were photographed through a Zeiss photomicroscope on Kodak® Panatomic X film developed in Microdol® developer. See FIGS. 2 and 3.

Chromosome counts were performed on five individuals from each treatment group and the control group. At least five well-spread unbroken metaphase cells from each individual were counted. If the initial chromosome counts indicated a polyploid individual, additional cells were counted to determine if the individual was a mosaic. The confidence interval for the percentage of ploidy in each treatment group was determined from the Steele-Torrie procedure.

The Results

Heat shocks used according to the method of this invention were successful in producing tetraploid, triploid, and mosaic channel catfish according to the following Table 1, wherein the percent polyploid for each temperature-duration combination was averaged over all postfertilization times.

TABLE 1

| Temp. (°C.) | Duration (min) | Hatch (%) Female 1 | Hatch (%) Female 2 | No. of Embryos Analyzed | Ploidy (%) 4n | Ploidy (%) 3n | Ploidy (%) 2n | Mosaic[1] |
|---|---|---|---|---|---|---|---|---|
| 43 | 1 | 0 | 73 | 15 | 7 | 0 | 60 | 33 |
|  | 2 | 0 | 0 | 1 | 0 | 0 | 0 | 100 |
|  | 3 | 0 | 0 | 0 | — | — | — | — |
|  | 4 | 0 | 0 | 0 | — | — | — | — |
| 42 | 1 | 40 | 78 | 30 | 7 | 7 | 77 | 10 |
|  | 2 | 11 | 0 | 2 | 0 | 0 | 100 | 0 |
|  | 3 | 0 | 0 | 0 | — | — | — | — |
|  | 4 | 0 | 0 | 0 | — | — | — | — |
| 41 | 1 | 55 | 82 | 29 | 0 | 7 | 93 | 0 |
|  | 2 | 46 | 84 | 30 | 3 | 3 | 67 | 27 |
|  | 3 | 38 | 42 | 26 | 62 | 0 | 8 | 31 |
|  | 4 | 6 | 0 | 10 | 40 | 0 | 50 | 10 |
| 40 | 1 | 53 | 79 | 30 | 0 | 13 | 87 | 0 |
|  | 2 | 54 | 86 | 25 | 0 | 12 | 88 | 0 |
|  | 3 | 46 | 71 | 30 | 0 | 13 | 67 | 20 |
|  | 4 | 35 | 76 | 30 | 10 | 7 | 50 | 33 |
| Control |  | 56 | 85 | 10 | 0 | 0 | 100 | 0 |
| Total |  |  |  | 268 |  |  |  |  |

[1]Mosaics with 4n/2n, 4n/3n/2n, and 5n/4n/2n cell types were observed.

Figure 2:
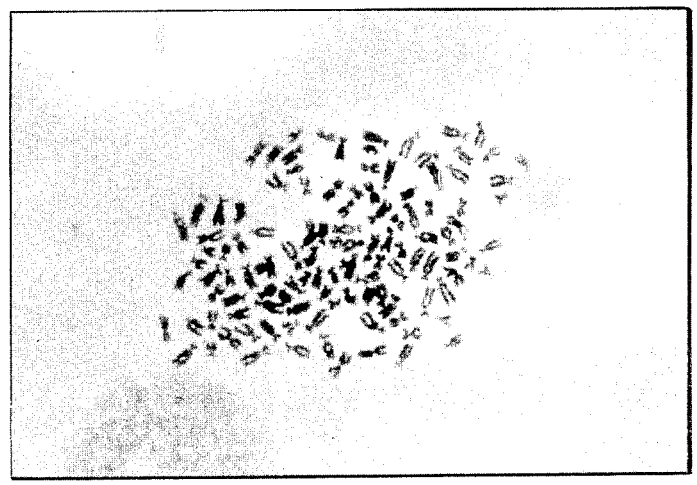
FIG. 2 is a microphotograph of a metaphase cell from a tetraploid channel catfish produced according to the method of the present invention showing the chromosomes of the cell.
Figure 3:
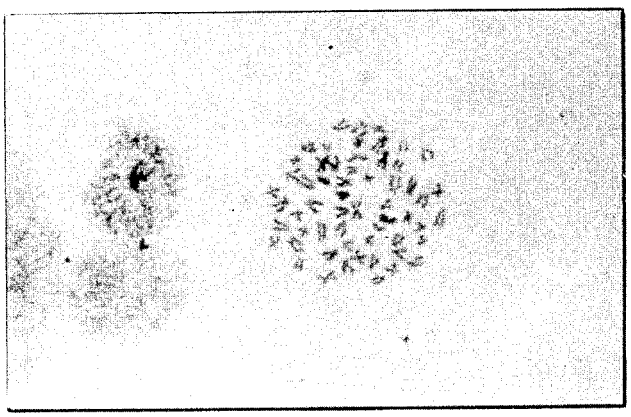
FIG. 3 is a microphotograph of a metaphase cell from a diploid channel catfish used as a control.

Tetraploid channel catfish cells should have contained 116 chromosomes but counts varied from 100 to 120 (FIG. 2). The control group developed normally and all fish analyzed from the control group were diploid (2 N=58; FIG. 3).

All eggs from female 1, including the controls, exhibited high mortality. It is believed that the high mortality rate was caused by the high iron content of the well water which caused iron precipitation on both the eggs and the baskets. The significant increase in hatchability in female 2 could have been due to the difference in eggs and/or water quality.

Hatchability was significantly greater in eggs treated with 40° C. and 41° C. shocks than with 42° C. and 43° C. shocks. Eggs heat-shocked at temperatures of 43° C. and 42° C. had complete mortality with shock durations greater than 2 minutes. The data were, therefore, analyzed in two separate sets; set 1 containing treatments of all postfertilization times, at 40° C. and 41° C. for 1, 2, 3 and 4 minute durations; and set 2 containing treatments of all postfertilization times at 40° C., 41° C., 42° C. and 43° C. for 1 and 2 minute durations.

Figure 4:
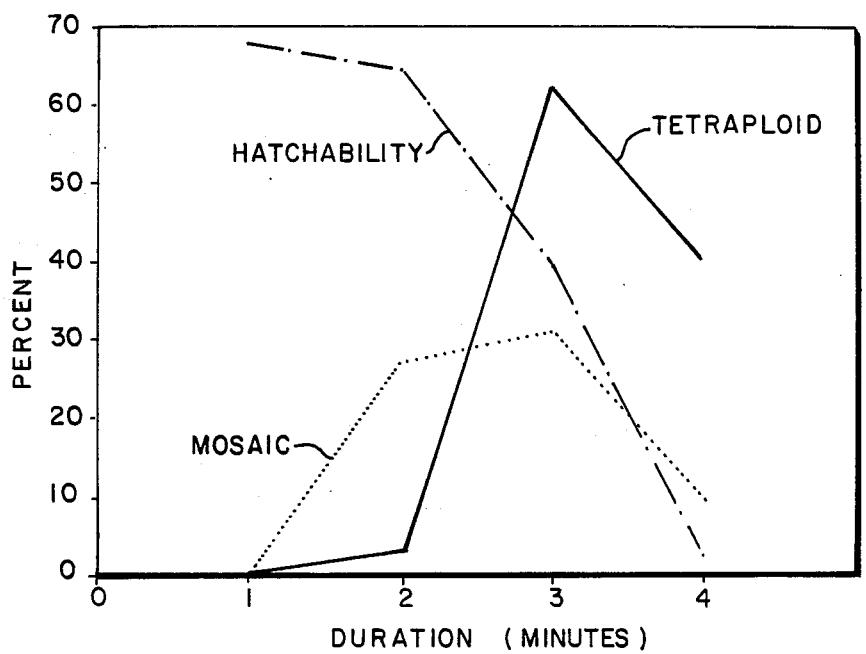
FIG. 4 is a graph showing the effect on polyploidy in channel catfish eggs of 41° C. heat shocks for durations of up to 4 minutes. All treatments are averaged for both females and for all postfertilization times.

Tetraploidy was induced at all temperatures tested but the incidence was highest at 41° C. The highest incidence of tetraploidy, 62%, was observed in embryos that had been heat shocked at 41° C. for 3 minutes. The effect on polyploidy in channel catfish eggs of 41° C. heat shocks at various durations up to 4 minutes is shown in FIG. 4, wherein all treatments are averaged over both females and postfertilization time.

Precise timing of the postfertilization shock was not a significant factor in set 1 shocks but in set 2 shocks, an 80-minute postfertilization shock was significantly more successful. Shocks of 4-minute duration had significantly lower hatchability than shocks of shorter durations in set 1. The decrease in tetraploidy at 4 minutes may have been due to the significant decrease in hatchability with 4 minute shocks as compared to shorter shocks. Fry that survived these shocks may have been at a more heat-tolerant stage of the cell cycle and not near division, thereby surviving the shock and remaining diploids.

Mosaics were found at all temperatures. Significantly more mosaics were found in set 1 for 4 minute shocks. A higher incidence of mosaicism was found at 43° C. for 1 or 2 minute shocks than for any other set 2 shock. Mosaics were likely the result of incomplete inhibition of mitosis in cells that had two or more nuclei and were possibly the result of retention of the second polar body.

Triploids were produced by heat shock only in the eggs of female 2. Eggs from this female were removed directly from the ovary and may not have been completely mature. Immature eggs may not have completed meiosis as quickly as mature oocytes. Heat shocks at 80 to 90 minutes postfertilization could have caused the polar body to be retained, thus producing a triploid. Thorgaard et al. found four triploids in a group of 18- month-old rainbow trout that had undergone heat shock to induce tetraploidy, as reported in "Triploid Rainbow Trout Identified By Flow Cytometry", *Aquaculture,* 29:305-309, 1982. The ripeness of the eggs, the stripping method, the sperm of the donor male, or the water quality may have contributed to the production of triploids by female 2.

The percentage hatchability for effective treatment combinations was low but no abnormalities were observed in sampled embryos or in growing fry. The tetraploid catfish produced by the method of this invention are as viable as their diploid full sibs and tolerate the polyploid condition well.

Tetraploidy would be useful in the production of sterile triploid off-spring in catfish production impoundments. Different species of catfish such as the white catfish, *Ictalurus catus,* and the blue catfish, *I. furcatus,* have been hybridized with channel catfish, as described in Bardach et al., "Aquaculture; the Farming and Husbandry of Fresh Water and Marine Organisms", Wiley and Sons, New York, 1972. Multivalent formation in meiosis I may be less likely because the chromosomes of blue catfish may be only partially homologous to channel catfish chromosomes. As reported in W. P. Muller, "Diplotene Chromosones of Hybrid *Xenopus* Oocytes", *Chromosoma* (Berlin), 59:273-282, 1977 meiotic pairing between homologous chromosomes would result in the production of diploid hybrid gametes. Triploid hybrids would also have the advantage of heterosis as well as triploidy.

The production of triploid hybrid catfish in commercial impoundments can be implemented without a major change in current management practices by breeding tetraploid channel catfish produced by the method of this invention with normal diploids. Rapid production of highly inbred lines will hasten selection of lines of fish with higher breeding values for important production traits such as growth rate and tolerance to water with low oxygen concentration. Selection pressure and the effects of triploidy and hybrid vigor also have the potential for improving the efficiency of catfish culture by producing food fish more highly adapted to intensive culture.

Although the procedures of this invention were developed using channel catfish these procedures are readily adaptable to other catfish species.

We claim:

1. A method for production of tetraploid channel catfish comprising the steps of:
   fertilizing an egg from a female channel catfish;
   incubating said fertilized egg for a first period of time, said first period of time ranging from the time required for first cell division cleavage of the fertilized egg to a time about ten minutes less than said time required for said first cell division cleavage;
   treating said fertilized egg by immersing said egg in water at a temperature of about 40° C. to about 43° C. for a second time period of about one to about four minutes;
   incubating the treated fertilized egg for a third period of time, said third period of time being sufficient to allow maturation of said fertilized egg to a tetraploid channel catfish fry.

2. The method of claim 1 wherein after incubation during the first period of time the fertilized egg is immersed in water at a temperature of about 41° C. for a period of about two to about four minutes.

3. The method of claim 1 wherein after incubating said fertilized egg for said first period of time the egg is treated by immersing it in water at a temperature of about 40° for about four minutes.

4. The method of claim 1 wherein the second time period is about two to about four minutes.

5. The method of claim 4 wherein the fertilized egg is incubated during said first period of time in water at about 27° C., and said first period of time is about 80 to about 90 minutes.

6. The method of claim 5 wherein the treated, fertilized egg is incubated during the third period of time in aerated flowing water at about 27° C. until the catfish fry are hatched.

7. The method of claim 5 wherein said fertilized egg is treated following said first period of time by immersion in water of a temperature of about 41° C. for about three to about four minutes.

8. The method of claim 1 wherein the fertilized egg is treated by immersing said egg in water at a temperature of about 42° C. to about 43° C. for about one minute.

* * * * *